US006777565B2

(12) United States Patent
Choi (10) Patent No.: US 6,777,565 B2
(45) Date of Patent: Aug. 17, 2004

(54) ORGANOMETALLIC COMPOUNDS AND THEIR USE AS PRECURSORS FOR FORMING FILMS AND POWDERS OF METAL OR METAL DERIVATIVES

(75) Inventor: Hyungsoo Choi, Champaign, IL (US)

(73) Assignee: Board of Trustees, The University of Illinois, Urbana, IL (US)

( * ) Notice: Subject to any disclaimer, the term of this patent is extended or adjusted under 35 U.S.C. 154(b) by 47 days.

(21) Appl. No.: 09/894,450

(22) Filed: Jun. 28, 2001

(65) Prior Publication Data

US 2002/0015789 A1 Feb. 7, 2002

Related U.S. Application Data

(60) Provisional application No. 60/214,988, filed on Jun. 29, 2000.

(51) Int. Cl.[7] .............................. C07F 7/02; C07F 9/00; C07C 16/00; C07C 14/26
(52) U.S. Cl. ................................ 556/9; 556/12; 556/13; 556/45; 556/136; 556/138; 427/587; 427/593
(58) Field of Search ................................ 556/9, 12, 13, 556/45, 136, 138; 427/587, 593

(56) References Cited

U.S. PATENT DOCUMENTS

| | | | |
|---|---|---|---|
| 3,088,361 A | | 5/1963 | Hallock .......................... 85/28 |
| 3,290,348 A | * | 12/1966 | Mullineaux ................... 556/13 |
| 3,458,547 A | * | 7/1969 | Coffey .......................... 556/23 |
| 4,645,849 A | * | 2/1987 | Lewis .......................... 556/16 |
| 4,814,294 A | | 3/1989 | West et al. .................. 437/200 |
| 5,587,651 A | | 12/1996 | Berkcan et al. ............. 437/200 |
| 5,605,865 A | | 2/1997 | Maniar et al. .............. 437/200 |
| 5,851,921 A | | 12/1998 | Gardner et al. ............. 430/655 |
| 6,037,001 A | | 3/2000 | Kaloyeros et al. .......... 427/250 |

FOREIGN PATENT DOCUMENTS

| | | | |
|---|---|---|---|
| GB | 717269 | | 2/1954 |
| JP | 1996000202661 | | 2/1998 |
| WO | WO199KR0000260 | | 2/1999 |
| WO | WO 92/02574 | * | 1/2002 |

OTHER PUBLICATIONS

Kruse et al., Chemical Communiations, No. 15, pp. 921–922 (1968).*
Levison et al., Journal of Chemical Society (A), pp. 96–99 (1970).*
Muetterties et al., Journal of American Chemical Society, vol. 104, No. 10, pp. 2940–2942 (1982).*
Gosser, Inorganic Chemistry, vol. 15, No. 6, pp. 1348–1351 (1976).*
ANderson et al., Inorganic Chemistry, vol. 21, No. 5, pp. 2095–2097 (1982).*
McEwen et al., Inorganic Chemistry, vol. 13, No. 12, pp. 2800–28–02 (1974).*
Muetterties et al., Journal of American Chemical Society, vol. 96, No. 26, pp. 7920–7926 (1974).*
Rakowski et al., Journal of American Chemical Society, vol. 99, No. 3, pp. 739–743 (1977).*
Muetterties et al., Journal of American Chemical Society, vol. 98, No. 15, pp. 4665–4667 (1976).*
Kruse, Walter, et al.: "Synthesis and configuration of hydrido(alkyl phosphito)–cobalt and–iron compounds" Chem. Commun., No. 15, 1968, pp. 921–922.
McEwen, G. K. et al.: "Preparation of hydriodnickel phosphites" Inorg. Chem., vol. 13, No. 12, 1974, pp. 2800–2802.
Gosser, L. W.: "Synthesis and properties of cobalt(1) compounds. 3. Hydridoacaloniriletris (triryl phosphite) cobalt complexes" Inor. Chem., vol. 16, No. 6, 1976, pp. 1348–1351.
Anderson, Lori, Beth, et al.: "Chemistry of transition–metal phosphine and phosphite complexes, 2, Preparation and properties of XHgCo'P(0C6H5)313L" Inor. Chem. (1982), 21(5), 2095–7, vol. 21, No. 5, 1982, pp. 2095–2097.
Carlton, Laurence: "Rhodium pentafluorophenylthiolate complexes derived from Rh2(.mu.–SC8F5)2(PPh3)4" J. Organomet. Chem., vol. 431, No. 1, 1982—2085, p. 2097.
Rakowski, M. C., et al.: "Low valent cobalt trisopropyl phosphite complexes. Characterization of a catalyst for the hydrogenation of alpha.,beta.–unsaturated ketones" J. Am. Chem. Soc., vol. 99, No. 3, 1977, pp. 739–743.
Muetterties, E. L. et al.: "Reductive elimination reactions" J. Am. Chem. Soc., vol. 98, No. 15, 1976, pp. 4685–4687.

(List continued on next page.)

Primary Examiner—Porfirio Nazario-Gonzalez
(74) Attorney, Agent, or Firm—Woodard, Emhardt, Moriarty, McNett & Henry LLP (57) ABSTRACT

Disclosed are organometallic compounds derived from Groups VIIb, VIII, IX, and X metals useful as precursors for the formation of metal containing powders and for the chemical deposition of the metals on substrates, particularly for the chemical vapor deposition of metal films suitable for the manufacture of electronic devices. Methods for their use are also disclosed. The preferred organometallic compounds of the present invention are of the formula $(R^1)_m M(PR^2{}_3)_x$, where M is a metal selected from the group consisting of manganese, technetium, rhenium, iron, cobalt, nickel, ruthenium, rhodium, palladium, osmium iridium and platinum wherein m is 0, 1, 2, 3 or 4; x is 2, 3, 4 or 5 and m+x are 2, 3, 4, 5, 6, 7 or 8, m and x selected according to each metals appropriate valence; each $R^1$ is independently selected from the group consisting of hydrogen, deuterium, $N_2$, $H_2$, $D_2$ and a variety of substituted alkyl groups; each $R^2$ is independently selected from the group consisting of lower alkyl, aryl, arylalkyl, and alkyl-Z, aryl-Z and arylalkyl-Z where Z is selected from the group consisting of oxy, silyl, siloxy, oxysilyl, siloxy, oxysiloxy, silyalkyl, oxysilylalkyl, siloxyalkyl, oxysiloxyalkyl, silylalkoxy, silylalkoxy, siloxyalkoxy and oxysiloxyalkoxy; and wherein when M is cobalt and one group $R^1$ is selected to be $N_2$, then m is 2 and the second group $R^1$ is hydrogen or deuterium.

16 Claims, 1 Drawing Sheet

OTHER PUBLICATIONS

Muetterties, E. L. et al.: "Chemistry of the transition metal–hydrogen bond. II. HCo'P(OR)314"J. Am. Chem. Soc., vol. 96, No. 26, 1974, pp. 7920–7926.

Muetterties, E. L. et al.: "Complexity in the reductive reaction of cobalt (ll) chloride In the presence of phosphiles. Isolation of stable, noninterconvertible Co'P(0CH3)314 and Co2'P (OCH3)318 molecules" J. Am. Chem. Soc., vol. 104, No. 10, 1982, pp. 2940–2942.

Levison, Jeffrey J. et al.: "Transition–metal complexes containing phosphorus ligands. 1. Triaryl phosphite complexes of cobalt and nickel" J. Chem. Soc. A, No. 1, 1970, pp. 96–99.

Database CA 'Online! Chemical Abstracts Service, Columbus, Ohio, US: Parshall, G. W.: "Homogeneous Catalytic activation of hydrocarbons" retrieved from STN Database accession No. 85:176606 abstract & Organotransition–Met. Chem., Proc. JPN.–AM Semin., 1ST (1975), Meeting Date 1974, 127–34. Editor(s): Ishii, Yoshio; Tsutsui, Minoru, Publisher: Plenum, New York, NY.

Chatt, J. et al.: "Hydrido–complexes of Iridium (lll) Stabllised by Tertiary Phosphines and Arsines" J. Chem. Soc. A, 1965, pp. 7391–7405.

Barefield, E. K., et al.: "Catalysis of Aromatic Hydrogen-–Deuterium Exchange by Metal Hydrides" J. Am. Chem. Soc, 92:17, 1970, pp. 5234–5236.

Titus, D. D., et al.: The Crystal and Molecular Structure of Hydridotatrakis (diethyl phenylphosphonite) cobelt (l), Chemical Communications, 1971, pp. 3622–323.

Lane, P. A. et al.: "Metal Organic CVD of Cobalt Thin Films Using Cobalt Tricarbonyl Nitrosyl" Chem. Vap. Deposition 1998, 4, No. 5, pp. 183–188.

Maruyama, T: "Cobalt Thim Films Prepared by Chemical Vapor Deposition from Cobalt Acetylacelonates" Jpn. J. Appl. Phys., vol. 36, 1997 Pt. 2, No. 6A, pp. L705–L707.

Gross, M.E., et al.: "Organometallic chemical vapor deposition of cobalt and formation of cobalt disilicide" J. Vac. Sci. Technol. B 6 (5), Sep./Oct. 1988, pp. 1548–1552.

Dormans, G.J.M., et al.: "OMCVD of cobalt and cobalt silicide" J. Crystal Growth, vol. 114, 1991, pp. 364–372.

Werner, H., et al.: "Synthesis and Reactivity of $OsH(n^2-CH_2PMe_2)(PMe_3)_3$ and of the Basic Dithydridoosmium Complex $cis-OsH_2(PMe_3)_4$" J. Am. Chem. Soc., No. 2 1983, pp. 547–549.

Gerlach, D. H., et al.: "Stereochemically Nonrigid Six–Coordinate Molecules. ll. Preparations and Reactions of Telrakis (organophosphorus) Metal Dihydride Complexes" J. Am. Chem. Soc., 94:13, 1972, pp. 4545–4549.

Smith, K. C., et al.: "Evaluation of precursors for chemical vapor deposition of ruthenium" Thin Solid Films, No. 378, 2000, pp. 73–81.

Meier, M., et al.: "Tetrakis (Triethyl Phosphite) Nickel (0), Palladium (0), and Platinum (0) Complexes" Inorganic Syntheses, vol. 13, 1972, pp. 112–116.

Titus, D., et al.: "Low–Valent Metal Complexes of Diathyl Phenylphosphonite" Inorganic Syntheses, vol. 13, 1972, p. 117.

Coulson, D. R.: "Tetrakis (Triphenylphosphine) Palladium (0)" Inorganic Syntheses, vol. 13, 1972, pp. 121–123.

Schunn, R. A.: Tetrakis (Triphenylphosphine) Nickel (0) Inorgaic Syntheses, vol. 13, 1972, p. 124.

Yoshida, T., et al.: "Two–Coordinate Phosphine Complexes of Palladium (0) and Platinum (0)" Inorganic Syntheses, vol. 19, 1979, pp. 101–111.

"Pentakis (Trimethyl Phosphite) Iron (0)" Inorganic Syntheses, vol. 120, 1980, pp. 79–81.

\* cited by examiner

ORGANOMETALLIC COMPOUNDS AND THEIR USE AS PRECURSORS FOR FORMING FILMS AND POWDERS OF METAL OR METAL DERIVATIVES

This application claims the benefit of provisional application 60/214,988 filed Jun. 29, 2000.

This invention was made with Government support under Contract Number CHE 73575 awarded by the National Science Foundation (NSF), and Contract Number N0014-98-1-0594 awarded by the Office of Naval Research (ONR). The Government has certain rights in the invention.

BACKGROUND OF THE INVENTION

This invention relates to organometallic compounds of metals of Groups VIIb, VIII, IX, and X including manganese, technetium, rhenium, iron, cobalt, nickel, ruthenium, rhodium, palladium, osmium, iridium and platinum and their uses in chemical vapor deposition (CVD) methods for depositing films of metal or metal derivatives on a substrate or forming a metal or metal derivative in powder form. More particularly the invention relates in preferred aspects to organometallic precursor compounds derived from metals of Groups VIIb, VIII, IX, and X especially suited for high purity deposition of the metal or a derivative such as, for example, a metal silicide, utilizing CVD techniques.

Metal silicides derived from metals of Groups VIIb, VIII, IX, and X are attractive compounds in the electronics field particularly regarding the manufacture of integrated circuits and micro-electronics. Interest in metal suicides is increasing as device scale-down progresses due to its good thermal and chemical stability, low resistivity, wide process window and its small lattice mismatch to the silicon crystal lattice, which allows the metal silicide to be grown epitaxially on silicon. Furthermore, the metal films derived from metals of Groups VIIb, VIII, IX, and X selectively deposited on silicon substrates can be made to form self-planarized epitaxial metal patterns whose surfaces are atomically flush with the surrounding silicon.

CVD is a particularly useful technique for deposition of metal and metal silicide films as compared to other methods of deposition such as plasma vapor deposition (PVD) methods like sputtering, e-beam evaporation, molecular beam epitaxy, and ion beam implantation. CVD can also be used to provide flexibility in the design of manufacturing electronic devices including the potential to reduce the number of processing phases required to provide a desired product.

To date, CVD of various metals has been hampered by the lack of suitable precursor compounds. For example, conventional cobalt organometallic CVD precursors, such as $Co(C_5H_7O_2)_2$, $Co(C_5H_7O_2)_3$, $Co_2(CO)_8$, $CO(C_5H_5)_2$, $Co(C_5H_5)(CO)_2$ and $Co(CO)_3(NO)$ have not demonstrated satisfactory properties for use in forming device-quality cobalt silicide films. $Co(C_5H_7O_2)_2$ and $Co(C_5H_7O_2)_3$ have low vapor pressures and therefore require high temperatures to produce a vapor flow sufficient to support CVD. $Co_2(CO)_8$ is significantly more volatile and can produce cobalt metal coatings without the addition of a reducing agent, but is too thermally unstable to be a practical CVD precursor, giving rise to competing side reactions and decomposition during storage, even under vacuum or an inert atmosphere. $Co(C_5H_5)_2$ and $Co(C_5H_5)(CO)_2$ may be used to deposit cobalt films, but such films can be subject to severe carbon and oxygen contamination problems, even when $H_2$ is used as a reducing agent. Likewise, $Co(CO)_3(NO)$ can be subject to unacceptable contamination with carbon and oxygen in the resulting cobalt and cobalt silicide layers when deposition is conducted at less than 350° C. or with a hydrogen flow of less than 500 standard cubic centimeters (sccm). Organometallic precursors based on the other metals in Groups VIb, VIII, IX, and X have demonstrated similar shortcomings.

Therefore there remains a need in the industry for precursor compounds derived from metals of Groups VIb, VIII, IX, and X suitable for CVD that can produce high purity, device-quality films of metals and/or metal derivatives such as, for example, metal silicide films. The present invention provides organometallic compounds which are well suited for such uses.

SUMMARY OF THE INVENTION

It is one object of the present invention to provide organometallic precursor compounds suitable for the chemical deposition of metals such as those of Groups VIIb, VIII, IX, and X. It is an object to provide preferred organometallic compounds of metals of Groups VIIb, VIII, IX, and X with relatively high vapor pressures and good thermal stability such that they are vaporizable without substantial decomposition. It is an object of one embodiment of the present invention to provide preferred organometallic compounds lacking metal-carbon bonds, which are suitable for use in chemical vapor deposition methods, whereby high purity metals or metal derivatives such as for example, metal suicides may be formed.

It is one object of another aspect of the present invention to provide novel organometallic compounds having relatively high vapor pressures and good thermal stability such that they are vaporizable without substantial decomposition.

It is one object of yet another aspect of the present invention to provide chemical deposition methods to deposit films of metal or metal derivatives derived from metals of Groups VIIb, VIII, IX, and X on various substrates, including silicon and gallium arsenide (GaAs) among others and to form metal and metal derivatives in powder form. It is an object of this aspect of the invention to provide preferred methods of producing metals and metal derivatives such as, for example, metal silcide as films of high purity, which particularly avoid contamination of the films by carbon and/or oxygen. It is a further object of this aspect of the present invention to provide preferred CVD methods useful in the fabrication of device-quality films based on metals of Groups VIIb, VIII, IX, and X or the metal's derivative, such as for example, a metal silicide or metal oxide.

Various of these and other objects are achieved by the organometallic phosphite and phosphine compounds according to the present invention and their use in deposition methods.

In one aspect of the present invention, films of metal and metal derivatives such as, for example, silicide are provided by the chemical deposition of metal or metal containing material on a substrate by contacting the substrate surface with an organometallic compound containing a Group VIb, VIII, IX or X metal and having the general formula I

I where M is a metal selected from a Group VIIb, VIII, IX or X metal wherein (a) when M is manganese, technetium or rhenium, m is 1; x is 5 and m+x is 6; (b) when M is iron, ruthenium or osmium, m is 0, 1, 2, 3 or 4; x is 2, 3, 4 or 5 and m+x is 4, 5, 6 or 7; (c) when M is cobalt, rhodium or iridium, m is 1, 2, 3 or 4 and x is 2, 3 or 4 and m+x is 4, 5, 6, 7 or 8; and (d) when M is nickel, palladium or platinum, m is 0 or 2, x is 2, 3 or 4 and m+x is 2, 3, 4, 5 or 6; each $R^1$ is independently selected from the group consisting of hydrogen, deuterium, $N_2$, $H_2$, $D_2$ and a group of the formula —$CR^3{}_2$—$CR^3{}_2$—$R^4$; each $R^2$ is independently selected from the group consisting of lower alkyl, aryl, arylalkyl, alkoxy, aryloxy, arylalkoxy, alkylsilyl, arylsilyl, arylalkylsilyl, alkoxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy; each $R^3$ is independently selected from the group consisting of hydrogen, deuterium, $C_1$–$C_6$ alkyl, $C_1$–$C_6$ cycloalkyl, phenyl, benzyl, ($C_1$–$C_2$ alkyl or alkoxy)$_3$-silyl, and ($C_1$–$C_2$ alkyl or alkoxy)$_3$-siloxy and wherein at least two groups $R^3$ are selected from the group consisting of hydrogen and deuterium; $R^4$ is hydrogen or deuterium; and wherein when M is cobalt, rhodium or iridium and one group $R^1$ is selected to be $N_2$, then m is 2 and the second group $R^1$ is hydrogen or deuterium. The preferred organometallic compounds of this embodiment of the invention are volatile and have good thermal stability in CVD processes, in that they can be vaporized without substantial decomposition.

In one aspect of the present invention, powders containing metal and/or metal derivatives are provided by the chemical decomposition of organometallic precursors upon dispersing a vapor or liquid into the medium, the vapor or liquid containing an organometallic compound of the formula $(R^1)_mM(PR^2{}_3)_x$, where M is a metal selected from a Group VIIb, VIII, IX or X metal wherein (a) when M is manganese, technetium or rhenium, m is 1; x is 5 and m+x is 6; (b) when M is iron, ruthenium or osmium, m is 0, 1, 2, 3 or 4; x is 2, 3, 4 or 5 and m+x is 4, 5, 6 or 7; (c) when M is cobalt, rhodium or iridium, m is 1, 2, 3 or 4 and x is 2, 3 or 4 and m+x is 4, 5, 6, 7 or 8; and (d) when M is nickel, palladium or platinum, m is 0 or 2, x is 2, 3 or 4 and m+x is 2, 3, 4, 5 or 6; each $R^1$ is independently selected from the group consisting of hydrogen, deuterium, $N_2$, $H_2$, $D_2$ and a group of the formula —$CR^3{}_2$—$CR^3{}_2$—$R^4$; each $R^2$ is independently selected from the group consisting of lower alkyl, aryl, arylalkyl, alkoxy, aryloxy, arylalkoxy, alkylsilyl, arylsilyl, arylalkylsilyl, alkoxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy; each $R^3$ is independently selected from the group consisting of hydrogen, deuterium, $C_1$–$C_6$ alkyl, $C_1$–$C_6$ cycloalkyl, phenyl, benzyl, ($C_1$–$C_2$ alkyl or alkoxy)$_3$-silyl, and ($C_1$–$C_2$ alkyl or alkoxy)$_3$-siloxy and wherein at least two groups $R^3$ are selected from the group consisting of hydrogen and deuterium; $R^4$ is hydrogen or deuterium; and wherein when M is cobalt, rhodium or iridium and one group $R^1$ is selected to be $N_2$, then m is 2 and the second group $R^1$ is hydrogen or deuterium. The preferred organometallic compounds of this embodiment of the invention are volatile and have good thermal stability in CVD processes, in that they can be vaporized without substantial decomposition.

"Organometallic" means a compound having at least one metal atom and at least one organic moiety. "Organic moiety," as used herein, means a portion of a molecule bonded to the remainder of the molecule, and including at least one carbon atom.

Preferred embodiments include, but are not limited to, depositing a metal film on an integrated circuit device work piece. Films comprised of metal derivatives, such as for example, a metal silicide, may be formed by annealing such metal films after deposition on the substrate, or alternatively, by conducting chemical vapor deposition with a mixture of a metal compound according to the present invention and one or more silicon chemical vapor deposition precursor compounds. Such metal and/or metal silicide films can be selectively deposited on an integrated circuit work piece to provide electrically conductive contacts on the work piece.

In preferred embodiments of the present invention:

a.) $R^1$ is hydrogen or deuterium, or, b.) m is 0.

The metal hydrides of these preferred embodiments advantageously lack metal-carbon bonds.

In another preferred embodiment, novel organometallic phosphite and phosphine compounds of formula I are provided wherein groups $R^2$ are not all the same moiety. In another preferred embodiment, at least one of groups $R^2$ contain a silicon atom, as for example, but without limitation, when $R^2$ is alkylsilyl, arylsilyl, arylalkylsilyl, alkoxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy.

In another aspect of the present invention, chemical deposition methods are provided for depositing metal, metal oxide and/or metal silicide films on a substrate by contacting the substrate surface with at least one metal precursor compound according to the present invention with the surface heated to a temperature at or above which the metal compound reacts to provide the film. In one embodiment of this aspect, the surface is heated to a temperature at or above the thermal decomposition temperature of the organometallic compound. In another embodiment, the surface facilitates the decomposition reaction of the organometallic compound at a temperature below the thermal decomposition temperature of the organometallic compound.

The metal precursor compounds of the present invention may also be adapted to liquid state chemical deposition methods as well as any known CVD method, with the conditions for a given application depending on the precursor compound used, the substrate being coated, and the thickness of metal film desired. For liquid phase delivery of metal compounds of the present invention, liquid metal precursor compounds can be delivered to the substrate surface neat or in a solvent compatible with the compound and substrate. Solid metal precursor compounds can be delivered in similarly compatible solvents. Any known liquid application methods can be adapted for use with the present metal compounds, including atomization and other liquid spray techniques.

In CVD methods, inert carrier gases and/or reducing agents, as for example, but without limitation, hydrogen may optionally be used with the present metal compounds in CVD methods. In preferred embodiments, device quality metal or metal silicide films may be produced.

Spray pyrolysis and the techniques described above can also be used without a substrate to deliver the precursor compounds into a medium such as nitrogen at a sufficient temperature to cause the formation of metals or metal derivatives in powder form. The metal powders produced in this manner, like the films deposited on substrates, are suited for high purity applications.

Related objects and advantages of the present invention will be apparent from the following detailed description of the preferred embodiments.

DESCRIPTION OF THE PREFERRED EMBODIMENTS

For the purposes of promoting an understanding of the principles of the invention, reference will now be made to specific preferred embodiments and specific language will be used to describe the same. It will nevertheless be understood that no limitation of the scope of the invention is thereby intended. Any alterations and modifications in the described invention, and any further applications of the principles of the invention as illustrated therein are contemplated as would normally occur to one skilled in the art to which the invention relates.

Typical CVD processes involve placing a substrate to be coated in a reaction chamber where the atmosphere can be controlled and introducing a gas flow that includes one or more vaporized precursor compounds and optionally an inert carrier gas and/or a co-reactant, such as a vaporized reducing agent. Typically, at least a portion of the substrate's surface is heated, most often to at least the thermal decomposition temperature of the precursor compound(s), whereupon the precursor compound(s) decompose upon contact with the surface and/or co-reactant(s) to deposit material on the substrate surface. Ideally, when the precursor compound decomposes, only the desired material is deposited and the remaining decomposition products remain in the vapor state and are evacuated or vented from the reaction chamber. In some, preferred CVD methods, the surface catalyzes, or otherwise facilitates the decomposition reaction, allowing the reaction to occur at the substrate surface at temperatures below the thermal decomposition temperature of the precursor compound(s). Many CVD processes use organometallic precursor compounds, which thermally or catalytically decompose at the heated substrate surface to deposit the metal or a metal containing material and release the organic moieties as vapors which are vented from the chamber. CVD processes include the conventional CVD processes, and other deposition processes utilizing chemical vapors such as, plasma assisted CVD and atomic layer deposition processes.

In desirable CVD processes, it is desirable that a CVD precursor compound be sufficiently volatile to generate a vapor pressure that can support CVD at a practical deposition rate. At the same time, it is desirable that the precursor be thermally stable at temperatures needed to generate the required vapor pressure. Likewise, the compound should be thermally stable enough to not decompose prematurely, before contacting the substrate, so as to maximize deposition of the product metal and minimize contaminants on the desired substrate surface. Lastly, for these desirable processes, it is desirable that the organic decomposition products remain in the vapor state and not react with the substrate or the metal-coated surface to avoid contamination of the coating.

In one embodiment of the present invention there is provided the use of organometallic compounds of metals of Groups VIIb, VIII, IX, and X in the deposition of metal films on desired substrates, wherein the compounds are volatile and have good thermal stability in CVD processes. Preferred organometallic compounds of the present invention are well suited for use in CVD processes in that they have sufficiently high vapor pressures to support CVD at practical deposition rates and are sufficiently thermally stable to be vaporizable without decomposing to a substantial degree.

Likewise, preferred organometallic compounds of the present invention decompose such that metal is deposited and the remaining decomposition products remain in the vapor state which advantageously renders them easily removable from the reaction chamber by venting or evacuating them out of the chamber.

It is to be understood that though the organometallic precursors of the present invention are well suited for use as precursor compounds in CVD processes, they may also be used to advantage in the liquid phase chemical deposition of metals on the surface of many solids. Those organometallic compounds which are liquids under reaction conditions, may be delivered to the substrate surface by any known techniques, either neat, or in a suitable solvent, as for example, but without limitation, atomization and other spray techniques, including, but not limited to electro-spray, as well as dipping the substrate into a liquid bath. Those organometallic compounds which are solid under reaction conditions may be delivered to the substrate surface in a suitable solvent. Methods for preparing metals and/or metal derivatives in powder form can utilize the standard CVD methods or any of the dispersal methods utilized to prepare films.

Preferred organometallic compounds of the present invention do not require reducing agents or carrier gases to produce metal films when used in CVD processes. However, reducing agents, as for example, but without limitation, hydrogen, may be used if desired as a co-reactant in CVD processes with the inventive metal precursor compounds.

In other embodiments of the present invention, other co-reactants, as for example, but without limitation, silane or disilane, may optionally be used with the present organometallic compounds to co-deposit a metal and other materials, or metal containing compounds, as for example but without limitation, metal suicides, on the substrate surface. In such methods, the vapor components can either be combined to provide a mixed feed whereby the components react with one another simultaneously or reacted sequentially to cause deposition of a metal or metal containing compound on the substrate surface, while the organic decomposition by-products remain in the vapor state and are evacuated from the reaction chamber.

For embodiments of the present invention involving CVD processes, preferred organometallic compounds are relatively volatile such that they have a vapor pressure sufficient to support the CVD process. Particularly preferred compounds are liquids at room temperature. In another embodiment, preferred compounds can be distilled or sublimed, either at ambient pressures or under vacuum at temperatures below their thermal decomposition temperatures. Particularly preferred compounds are distillable or sublimable at or below a temperature of about 200° C. and a pressure of about 0.05 mm Hg, more preferably, at or below 150° C. and 0.05 mm Hg.

Likewise for embodiments of the present invention involving CVD processes, the high end of the thermal or catalytic decomposition temperature for the organometallic compound is dictated by the thermal stability of the substrate; the decomposition temperature, or temperature at which the substrate surface would catalytically decompose the compound, is preferably below the temperature at which the substrate would melt, decompose or otherwise be adversely effected. These temperatures are well known to those skilled in the art or are readily ascertainable by standard techniques. Thermal decomposition temperatures for preferred organometallic compounds of the present invention are significantly above a temperature at which the compound's vapor pressure is sufficient to support CVD, but below the temperature at which damage to the substrate would occur. Preferred thermal decomposition temperatures are between about 100° C. and about 700° C., and more particularly between about 130° C. and about 400° C.

Preferred organometallic precursor compounds according to the present invention are of the formula I, $(R^1)_m M(PR^2_3)_x$      I where:
(1) M is a metal selected from the group consisting of manganese, technetium, rhenium, iron, ruthenium, osmium, nickel, palladium, and platinum; each $R^1$ is independently selected from the group consisting of hydrogen, deuterium, $H_2$, $D_2$ and a group of the formula $-CR^3_2-CR^3_2-R^4$, each $R^2$ is independently selected from the group consisting of arylalkyl, arylalkoxy, alkylsilyl, arylsilyl, arylalkylsilyl, alkoxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy; each $R^3$ is independently selected from the group consisting of hydrogen, deuterium, $C_1$–$C_6$ alkyl, $C_1$–$C_6$ cycloalkyl, phenyl, benzyl, ($C_1$–$C_2$ alkyl or alkoxy)$_3$-silyl, and ($C_1$–$C_2$ alkyl or alkoxy)$_3$-siloxy and wherein at least two groups $R^3$ are selected from the group consisting of hydrogen and deuterium; $R^4$ is hydrogen or deuterium; and wherein (a) when M is manganese, technetium or rhenium, m is 1, x is 5 and m+x is 6 and wherein said $R^2$ groups are not all the same; (b) when M is iron, ruthenium or osmium m is 0, 1, 2, 3 or 4; x is 2, 3, 4 or 5 and m+x is 4, 5, 6 or 7; and wherein said $R^2$ groups are not all the same; and (c) when M is nickel, palladium or platinum m is 0 or 2, x is 2, 3 or 4 and m+x is 2, 3, 4, 5 or 6, and wherein said $R^2$ groups are not all the same;

(2) M is a metal selected from the group consisting of rhodium and iridium; m is 1, 3 or 4; x is 2, 3 or 4; and m+x is 4, 5, 6, 7 or 8; each $R^1$ is independently selected from the group consisting of hydrogen, deuterium, $N_2$, $H_2$, $D_2$ and a group of the formula $-CR^3_2-CR^3_2-R^4$; each $R^2$ is independently selected from the group consisting of arylalkyl, alkoxy, aryloxy, arylalkoxy, alkylsilyl, arylsilyl, arylalkylsilyl, alkoxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy; each $R^3$ is independently selected from the group consisting of hydrogen, deuterium, $C_1$–$C_6$ alkyl, $C_1$–$C_6$ cycloalkyl, phenyl, benzyl, ($C_1$–$C_2$ alkyl or alkoxy)$_3$-silyl, and ($C_1$–$C_2$ alkyl or alkoxy)$_3$-siloxy and wherein at least two groups $R^3$ are selected from the group consisting of hydrogen and deuterium; $R^4$ is hydrogen or deuterium; and wherein said $R^2$ groups are not all the same; or (3) M is cobalt; m is 1, 2, or 3; x is 3 or 4; m+x is 5 or 6; each $R^1$ is independently selected from the group consisting of hydrogen, deuterium, $N_2$, $H_2$, $D_2$ and a group of the formula $-CR^3_2-CR_2-R^4$; each $R^2$ is independently selected from the group consisting of lower alkyl, aryl, arylalkyl, alkoxy, aryloxy, arylalkoxy, alkylsilyl, arylsilyl, arylalkylsilyl, alkoxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy; each $R^3$ is independently selected from the group consisting of hydrogen, deuterium, $C_1$–$C_6$ alkyl, $C_1$–$C_6$ cycloalkyl, phenyl, benzyl, ($C_1$–$C_2$ alkyl or alkoxy)$_3$-silyl, and ($C_1$–$C_2$ alkyl or alkoxy)$_3$-siloxy and wherein at least two groups $R^3$ are selected from the group consisting of hydrogen and deuterium; $R^4$ is hydrogen or deuterium; and wherein when one group $R^1$ is selected to be $N_2$, then m is 2 and the second group $R^1$ is hydrogen or deuterium; and wherein said $R^2$ groups are not all the same.

The size and degree of branching of groups $R^1$ and $R^2$ can effect the volatility of the organometallic compound and it's thermal decomposition characteristics, including the volatility of the organic decomposition by-products. Selection of $R^1$ and $R^2$ can be manipulated to derive precursor compounds with desired vapor pressures at a given temperature. Preferred alkyl and alkoxy moieties are branched or unbranched $C_1$–$C_6$ alkyl and alkoxy. As used herein, aryl means a hydrocarbon moiety including an aromatic 6-carbon ring or condensed aromatic 6-carbon rings and optionally having alkyl substitutions on the ring(s). Preferred aryl is one 6-carbon ring, optionally having one or two $C_1$–$C_3$ alkyl substitutions thereon. As used herein, alkyl, aryl or alkoxy moiety means any distinct hydrocarbon portion of $R^1$ or $R^2$, as for example, alkylsilylalkyl containing two distinct alkyl moieties, each bonded directly to the same silicon atom.

Particularly preferred organometallic precursor compounds of formula I are those wherein:

a.) $R^1$ is hydrogen or deuterium or, b.) m is 0.

These embodiments do not contain any metal-carbon bonds. It has been surprisingly found that eliminating direct metal-carbon bonds in an organometallic precursor compound significantly decreases the potential for contamination of the resulting metal film by carbon and/or oxygen.

For those embodiments of organometallic compounds of the present invention derived from metals of Group IX where one $R^1$ group is selected to be $N_2$, m is then 2 and the second $R^1$ group is hydrogen. The bonding of the $N_2$ moiety is through pi bonding of the moiety as a whole to the metal atom, as opposed to sigma or sp hybrid bonding of one nitrogen atom to metal.

For those embodiments of organometallic compounds of the present invention where $R^1$ is a group of the formula —$CR^3{}_2$—$CR^3{}_2$—$R^4$, $R^4$ is hydrogen or deuterium. As such, $R^1$ is an organic group with a tautomerizable β-hydrogen or β-deuterium. Without being bound to a particular theory, these $R^1$ groups are thought to exist in two tautomeric forms, one with the $R^1$ group bond to the metal through sp hybrid bonding to the α-carbon, and the other with the $R^4$ β-hydrogen or β-deuterium displacing to the metal atom as a hydride and the resulting α,β-carbon-carbon double-bonding to the metal atom through pi bonding. It is believed that such a tautomeric carbon-metal bonding enhances the ability of these metal compounds to decompose to deposit metal on a substrate surface, while greatly reducing the potential for contamination of the resulting metal film with carbon.

Preferred $R^2$ groups are those wherein any alkyl moiety is $C_1$–$C_6$ alkyl, any aryl moiety is phenyl or $C_1$–$C_3$ mono- or di-substituted phenyl, and any alkoxy moiety is $C_1$–$C_6$ alkoxy.

Also particularly preferred are organometallic compounds wherein at least one of the $R^2$ groups contains at least one silicon atom. Preferred silicon containing $R^2$ groups include alkylsilyl, arylsilyl, arylalkylsilyl, alloxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy. It has been surprisingly found that several of these compounds are liquids at room temperature, having acceptably high vapor pressures for CVD and exhibit favorable thermal stability in CVD processes.

Organometallic compounds wherein at least one of the $R^2$ groups is selected to be alkylsilyl, arylsilyl, arylalkylsilyl, alkoxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, or arylalkoxysiloxyalkoxy, and wherein $R^1$ is hydrogen or deuterium are yet more preferred.

It is to be understood that any silicon atom in an organometallic compound of the present invention will have four substituents bound to it, and that preferred compounds are those in which none of the silicon-bound substituents are hydrogen or deuterium.

Suitable organometallic precursor compounds include, but are not limited to the following:

Exemplary compounds with C—Co bonds:

$(CH_3CH_2)Co(P(CH_3)_3)_3$,
$(CH_3CH_2)Co[P(OCH_3)_3]_3$,
$(C_4H_9)Co[P(OCH_3)_3]_3$,
$(C_6H_5-CH_2CH_2)Co[P(OCH_3)_3]_3$,
$((CH_3)_3SiCH_3CH_2)Co[P(OCH_3)_3]_3$,
$((OCH_3)_3SiOCH_3CH_2)Co[P(OCH_3)_3]_3$;

Preferred silyl phosphite compounds with C—Co bonds:

$(C_2H_5)Co[(CH_3O)_3SiOP(OCH_3)_2]_4$,
$(C_2H_5)Co[(CH_3)_3Si-P(CH_3)_2]_4$,
$(C_2H_5)Co[(CH_3)_3SiOP(OCH_3)_2]_4$;

Preferred organometallic precursor compounds of formula I wherein $R^1$ is hydrogen and M is iron, ruthenium or osmium are:

$H_2M[P(OCH_3)_3]_4$,
$H_2M[P(OC_2H_5)_3]_4$,
$H_2M[P(OC_3H_7)_3]_4$,
$H_2M[P(OCH(CH_3)_2)_3]_4$,
$H_2M[P(OC_4H_9)_3]_4$,
$H_2M[P(OCH(CH_3)(CH_2CH_3))_3]_4$,
$H_2M[P(OCH_2CH(CH_3)_2)_3]_4$,
$H_2M[(C_6H_5)OP(OCH_3)_2]_4$,
$H_2M[(C_6H_5)OP(OC_2H_5)_2]_4$,
$H_2M[(C_6H_5)CH_2OP(OCH_3)_2]_4$,
$H_2M[(C_6H_5)CH_2OP(OC_2H_5)_2]_4$,
$H_2M[(C_3H_7)OP(OCH_3)_2]_4$,
$H_2M[(CH_3)_3COP(OC_2H_5)_2]_4$,
$H_2M[(CH_3)OP(OC_2H_5)_2]_4$
$H_2M[(C_2H_5)OP(OCH_3)_2]_4$,
$H_2M[(C_4H_9)OP(OC_2H_5)_2]_4$,
$H_2M[(C_4H_9)OP(OCH_3)_2]_4$,
$H_2M[(CH_3)_3SiOP(OCH_3)_2]_4$,
$H_2M[(CH_3)_3SiOP(OC_2H_5)_2]_4$,
$H_2M[(C_2H_5)_3SiOP(OCH_3)_2]_4$,
$H_2M[(C_2H_5)_3SiOP(OC_2H_5)_2]_4$,

Preferred organic precursor compounds of formula I wherein m is 0 and M is iron, ruthenium or osmium are.

$M[(C_6H_5)OP(OCH_3)_2]_5$,
$M[(C_6H_5)OP(OC_2H_5)_2]_5$,
$M[(C_6H_5)CH_2OP(OCH_3)_2]_5$,
$M[(C_6H_5)CH_2OP(OC_2H_5)_2]_5$,
$M[(C_3H_7)OP(OCH_3)_2]_5$,
$M[(C_4H_9)OP(OC_2H_5)_2]_5$,
$M[(CH_3)OP(OC_2H_5)_2]_5$,
$M[(C_2H_5)OP(OCH_3)_2]_5$,
$M[(C_4H_9)OP(OCH_3)_2]_5$
$M[(CH_3)_3SiOP(OCH_3)_2]_5$,

M[(CH₃)₃SiOP(OC₂H₅)₂]₅,
M[(C₂H₅)₃SiOP(OCH₃)₂]₅,
M[(C₂H₅)₃SiOP(OC₂H₅)₂]₅;
Preferred organometallic precursor compounds of formula I wherein R¹ is hydrogen and M is cobalt are:
HCo[P(OCH₃)₃]₄,
HCo[P(OC₂H₅)₃]₄,
HCo[P(OC₃H₇)₃]₄,
HCo[P(OCH(CH₃)₂)₃]₄,
HCo[P(OC₄H₉)₃]₄,
HCo[P(OCH(CH₃)(CH₂CH₃))₃]₄,
HCo[P(OCH₂CH(CH₃)₂)₃]₄,
HCo[(C₆H₅)OP(OCH₃)₂]₄,
HCo[(C₆H₅)OP(OC₂H₅)₂]₄,
HCo[(C₆H₅)CH₂OP(OCH₃)₂]₄,
HCo[(C₆H₅)CH₂OP(OC₂H₅)₂]₄,
HC[(C₃H₇)OP(OCH₃)₂]₄,
HCo[(CH₃)₃COP(OC₂H₅)₂]₄,
HCo[(CH₃)OP(OC₂H₅)₂]₄
HCo[(C₂H₅)OP(OCH₃)₂]₄,
HCo[(C₄H₉)OP(OC₂H₅)₂]₄,
HCo[(C₄H₉)OP(OCH₃)₂]₄,
HCo[(CH₃)₃SiOP(OCH₃)₂]₄,
HCo[(CH₃)₃SiOP(OC₂H₅)₂]₄,
HCo[(C₂H₅)₃SiOP(OCH₃)₂]₄,
HCo[(C₂H₅)₃SiOP(OC₂H₅)₂]₄;
Preferred organometallic precursor compounds of formula I wherein R¹ is hydrogen and M is rhodium are:
HRh[P(OCH₃)₃]₄,
HRh[P(OC₂H₅)₃]₄,
HRh[P(OC₃H₇)₃]₄,
HRh[P(OCH(CH₃)₂)₃]₄,
HRh[P(OC₄H₉)₃]₄,
HRh[P(OCH(CH₃)(CH₂CH₃))₃]₄,
HRh[P(OCH₂CH(CH₃)₂)₃]₄,
HRh[(C₆H₅)OP(OCH₃)₂]₄,
HRh[(C₆H₅)OP(OC₂H₅)₂]₄,
HRh[(C₆H₅)CH₂OP(OCH₃)₂]₄,
HRh[(C₆H₅)CH₂OP(OC₂H₅)₂]₄,
HRh[(C₃H₇)OP(OCH₃)₂]₄,
HRh[(CH₃)₃COP(OC₂H₅)₂]₄,
HRh[(CH₃)OP(OC₂H₅)₂]₄
HRh[(C₂H₅)OP(OCH₃)₂]₄,
HRh[(C₄H₉)OP(OC₂H₅)₂]₄,
HRh[(C₄H₉)OP(OCH₃)₂]₄,
HRh[(CH₃)₃SiOP(OCH₃)₂]₄,
HRh[(CH₃)₃SiOP(OC₂H₅)₂]₄,
HRh[(C₂H₅)₃SiOP(OCH₃)₂]₄,
HRh[(C₂H₅)₃SiOP(OC₂H₅)₂]₄;
Preferred organometallic precursor compounds of formula I wherein R¹ is hydrogen and M is iridium are:
H₃Ir[P(OCH₃)₃]₃,
H₃Ir[P(OC₂H₅)₃]₃,
H₃Ir[P(OC₃H₇)₃]₃,
H₃Ir[P(OCH(CH₃)₂)₃]₃,
H₃Ir[P(OC₄H₉)₃]₃,
H₃Ir[P(OCH(CH₃)(CH₂CH₃))₃]₃,
H₃Ir[P(OCH₂CH(CH₃)₂)₃]₃,
H₃Ir[(C₆H₅)OP(OCH₃)₂]₃
H₃Ir[(C₆H₅)OP(OC₂H₅)₂]₃,
H₃Ir[(C₆H₅)CH₂OP(OCH₃)₂]₃,
H₃Ir[(C₆H₅)CH₂OP(OC₂H₅)₂]₃,
H₃Ir[(C₃H₇)OP(OCH₃)₂]₃,
H₃Ir[(CH₃)₃COP(OC₂H₅)₂]₃,
H₃Ir[(CH₃)OP(OC₂H₅)₂]₃
H₃Ir[(C₂H₅)OP(OCH₃)₂]₃,
H₃Ir[(C₄H₉)OP(OC₂H₅)₂]₃,
H₃Ir[(C₄H₉)OP(OCH₃)₂]₃,
H₃Ir[(CH₃)₃SiOP(OCH₃)₂]₃,
H₃Ir[(CH₃)₃SiOP(OC₂H₅)₂]₃,
H₃Ir[(C₂H₅)₃SiOP(OCH₃)₂]₃,
H₃Ir[(C₂H₅)₃SiOP(OC₂H₅)₂]₃
H₅Ir[(CH₃)₃SiOP(OCH₃)₂]₂,
H₅Ir[(CH₃)₃SiOP(OC₂H₅)₂]₂,
H₅Ir[(C₂H₅)₃SiOP(OCH₃)₂]₂,
H₅Ir[(C₂H₅)₃SiOP(OC₂H₅)₂]₂,
Preferred organometallic precursor compounds of formula I wherein m is 0 and M is nickel, palladium or platinum are:
M[(C₆H₅)OP(OCH₃)₂]₂,
M[(C₆H₅)OP(OC₂H₅)₂]₂,
M[(C₆H₅)CH₂OP(OCH₃)₂]₂,
M[(C₆H₅)CH₂OP(OC₂H₅)₂]₂,
M[(C₃H₇)OP(OCH₃)₂]₂,
M[(C₄H₉)OP(OC₂H₅)₂]₂,
M[(CH₃)OP(OC₂H₅)₂]₂,
M[(C₂H₅)OP(OCH₃)₂]₂,
M[(C₄H₉)OP(OCH₃)₂]₂,
M[(C₆H₅)OP(OCH₃)₂]₃,
M[(C₆H₅)OP(OC₂H₅)₂]₃,
M[(C₆H₅)CH₂OP(OCH₃)₂]₃,
M[(C₆H₅)CH₂OP(OC₂H₅)₂]₃,
M[(C₃H₇)OP(OCH₃)₂]₃,
M[(C₄H₉)OP(OC₂H₅)₂]₃,
M[(CH₃)OP(OC₂H₅)₂]₃,
M[(C₂H₅)OP(OCH₃)₂]₃,
M[(C₄H₉)OP(OCH₃)₂]₃;
M[P(OCH₃)₃]₄,
M[P(OC₂H₅)₃]₄,
M[P(OC₃H₇)₃]₄,
M[P(OCH(CH₃)₂)₃]₄,
M[P(OC₄H₉)₃]₄,
M[P(OCH(CH₃)(CH₂CH₃))₃]₄,
M[P(OCH₂CH(CH₃)₂)₃]₄,
M[(C₆H₅)OP(OCH₃)₂]₄,
M[(C₆H₅)OP(OC₂H₅)₂]₄,
M[(C₆H₅)CH₂OP(OCH₃)₂]₄,
M[(C₆H₅)CH₂OP(OC₂H₅)₂]₄,
M[(C₃H₇)OP(OCH₃)₂]₄,
M[(CH₃)₃COP(OC₂H₅)₂]₄,
M[(CH₃)OP(OC₂H₅)₂]₄
M[(C₂H₅)OP(OCH₃)₂]₄,
M[(C₄H₉)OP(OC₂H₅)₂]₄,
M[(C₄H₉)OP(OCH₃)₂]₄,
M[(CH₃)₃SiOP(OCH₃)₂]₄, $M[(CH_3)_3SiOP(OC_2H_5)_2]_4$,
$M[(C_2H_5)_3SiOP(OCH_3)_2]_4$,
$M[(C_2H_5)_3SiOP(OC_2H_5)_2]_4$;

as well as analogs substituting deuterium in place of any hydrogen.

In another aspect of the present invention, novel metal organophosphites and phosphines derived from manganese, technetium, rhenium, iron, ruthenium, osmium, cobalt, rhodium, iridium, nickel palladium and platinum are provided. The novel organometallic compounds of this aspect of the present invention are of formula I, wherein the R groups are not all the same. Preferred compounds of this aspect of the invention are cobalt compounds wherein at least one group $R^2$ is alkylsilyl, arylsilyl, arylalkylsilyl, alkoxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy. Particularly preferred compounds of this aspect of the invention are those in which $R^1$ is hydrogen or deuterium.

This new class of organometallic compounds can be synthesized by preparing the mixed phosphite or phosphine, followed by reaction with a metal salt, as for example, but without limitation, $CoCl_2$. By way of example, a mixed phosphite can be synthesized by reacting phosphorus trichloride in a suitable organic solvent in two or three cycles with the alcohols of the desired R groups in equimolar ratio with a proton scavenger. One non-limiting illustration would be to react $PCl_3$ in diethyl ether at $-78°$ C. with 1 molar equivalent of ethanol and 1 molar equivalent of dimethylaniline. After the reaction has run to completion, a second aliquot of 2 molar equivalents of both methanol and dimethylaniline are added and the second reaction run to completion at room temperature to produce ethyldimethyl phosphite. The ethyldimethyl phosphite in an appropriate solvent, such as glyme, can then be reacted with $CoCl_2$ in the presence of NaBH4 to produce $HCo[C_2H_5OP(OCH_3)_2]_4$. The cobalt organometallics can then be purified by art recognized means, as for example by extraction with organic solvents and batch adsorption and elution from neutral alumina, followed by a final distillation or sublimation step. Similar salts of metals from Groups VIb, VIII, IX or X can be utilized in this manner to prepare organometallic compounds suitable for CVD applications.

The organometallic precursor compounds of the present invention can be used in conventional CVD apparatuses using known CVD techniques to produce metal and/or metal silicide films on desired substrates. The films produced using the organometallic compounds of the present invention as CVD precursors can be substantially free of carbon and oxygen contamination. Substrates of particular interest include those comprised of silicon, gallium arsenide (GaAs), silicon carbide, silicon nitride, germanium, as well as various multilayer substrates, such as titanium and titanium nitride coated silicon and silicon on sapphire (sos), or any other substrate configuration used in the manufacture of electronic devices, particularly microelectronic components such as integrated circuits. Other suitable substrates include ceramic surfaces, for example, but without limitation, $SiO_2$, $SiO_xN_y$, $Al_2O_3$, $TiO_2$, MgO, $Ta_2O_5$, and ITO (indium tin oxide), as well as mixed metal oxides and polymer surfaces.

In one embodiment of the present invention, metal or metal containing films are deposited on at least a portion of the surface of a desired substrate by contacting the surface or portion thereof with an organometallic compound of the present invention. In one instance, the organometallic compound is in the liquid phase as it contacts the substrate surface. In a preferred embodiment, the organometallic compound is vaporized, the substrate surface, or portion thereof, is contacted with the vapor, the compound decomposed and a metal or metal derivative is deposited on the substrate or portion thereof. In one embodiment, the reaction includes a thermal decomposition of the organometallic compound at the substrate surface, as for example, but without limitation, by contacting the substrate surface with a vaporized organometallic compound of the present invention when the substrate surface or portion thereof is at a temperature at or above the thermal decomposition temperature for the organometallic compound. In a second embodiment, the reaction includes a decomposition reaction catalyzed or otherwise facilitated by the substrate surface when the substrate surface or portion thereof is at a temperature below the thermal decomposition temperature for the organometallic compound.

In a typical CVD embodiment of the present invention, a substrate to be coated is cleaned and placed in a CVD vacuum chamber, which is then flushed with an inert gas and evacuated. The precursor is maintained at a desired temperature in a reagent source chamber. A controlled stream of precursor compound in the vapor state is introduced into the CVD chamber through a regulated feed line from the reagent source chamber and carried past the substrate, optionally with the aid of an inert carrier gas stream, as for example, but without limitation argon, nitrogen, helium, xenon or the like. The substrate is heated to a temperature at which the precursor compound reacts on the substrate, whether by thermal decomposition or by a substrate facilitated decomposition reaction, to deposit the Group VIIb, VIII, IX or X metal, releasing the remaining reaction products into the vapor phase, where they are then evacuated from the chamber as a waste product.

As is well known in the art, the substrate can be heated as a whole to produce a uniform coating of metal or metal containing material, as for example, but without limitation, a metal silicide, over the entire exposed surface. Alternatively, as is also known in the art, small, specific areas on the substrate surface can be heated to the desired substrate temperature, as for example with a scanning focused laser beam, to coat only the specific areas heated with metal or metal containing material. The films obtained can be patterned either during the deposition or after by any number of methods as are familiar to those skilled in the art.

Advantageous, substrate temperatures may range between about 100° C. and about 700° C., preferably between about 120° C. and about 500° C., and more preferably between about 130° C. and about 400° C. Advantageous cobalt precursor feed temperatures may range between about 25° C. and about 200° C., preferably between about 40° C. and about 170° C. These ranges are by way of example, rather than limitation. The optimum temperature will depend on the substrate and organometallic precursor used, as well as the reaction conditions, including the pressures in the precursor source chamber and reaction chamber. For example, feed and/or substrate temperatures for solid metal precursor compounds may be higher than the ranges above, while liquid precursor compounds, particularly if under relatively high vacuum, may be lower than the above ranges.

The deposition time required to produce a film of a desired thickness is easily calculated after a determination of the rate of deposition for a given compound at a given temperature with a given substrate and substrate temperature, and optionally with a given carrier gas stream flow rate and/or reducing reagent concentration. By way of example, but without limitation, typical deposition times may range between about 10 minutes and about 24 hours or more typically between about 10 minutes and about 60 minutes.

Prior to heating the substrate or the beginning of the deposition, the system is preferably purged with a non-reactive gas such as argon, nitrogen, helium, xenon or the like. Though not a necessity, it is preferred to evacuate the reaction chamber prior to deposition. During the deposition, the pressure in the reactor is typically maintained at a partial vacuum, as for example, but without limitation, at a pressure of about 0.1 to about 10 mm Hg when a carrier gas is used. System pressures when no carrier gas is used are generally lower, as for example, but without limitation, between about 0.01 and 0.1 mm Hg and can be as low as $10^{-12}$ to about $10^{-6}$ when ultra-high vacuums are utilized. The rate of deposition is dependent on the whole of the combination of reaction conditions used, including the pressure and the use or non-use of a carrier gas.

When silicon is the substrate being coated, the initial metal film can optionally be subjected to an annealing process, as is well known in the art, to convert at least a portion of the metal to a metal silicide. In other embodiments the deposited metal film is not treated to form a corresponding silicide, instead being used in its pure form.

Alternatively, as is also known in the art, silicon can be co-deposited with the metal by CVD using a suitable silicon precursor compound, such as silane or disilane, under conditions where a metal silicide is formed on the substrate surface directly. Co-deposition of silicon with a metal may be used to form metal silicide films on non-silicon substrates, such as GaAs, as well as on silicon surfaces. Metal silicides can be formed on a silicone substrate by co-deposition of silicon and a metal on a silicon substrate or by deposition of a metal onto the substrate followed by an annealing step.

It would likewise be possible to co-deposit other compounds with the metal by including an appropriate precursor compound in the vapor feed to the CVD reaction chamber.

Figure 1:
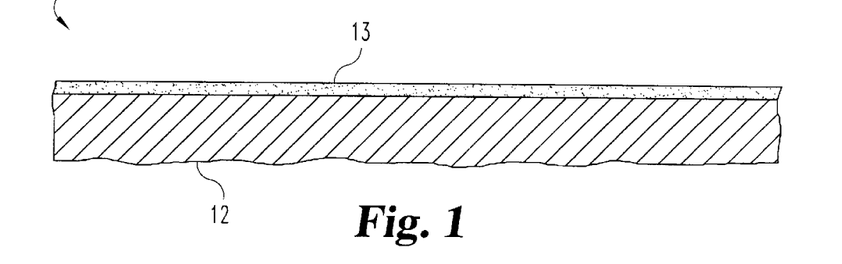
FIG. 1 is a schematic cross section of a substrate with a metal film thereon or a film thereon derived from a metal derivative such as, for example, a metal suicide.

In another aspect of the present invention, a film is provided which includes a metal or a metal containing compound, which film is obtainable by contacting an organometallic compound of the present invention with a substrate surface to deposit metal or a metal containing compound thereon. In a preferred embodiment of this aspect of the invention, the decomposition includes contacting the organometallic compound with the surface when the surface or a portion thereof desired to be coated is heated to a temperature at which the organometallic compound decomposes upon contact, whether by thermal decomposition, at or above the compound's thermal decomposition temperature, or by catalysis or other facilitation of the substrate surface or precursor molecule, at a temperature below the thermal decomposition temperature of the compound, as for example, but without limitation, in a CVD process. FIG. 1 (not to scale) shows a schematic diagram of such a film 14, where surface 12 of substrate 10 has been coated with metal or a metal containing compound 13 by reaction with an organometallic compound of the present invention. In a preferred embodiment, film 14 is characterized by being substantially free of contamination by carbon and/or oxygen.

Figure 2:
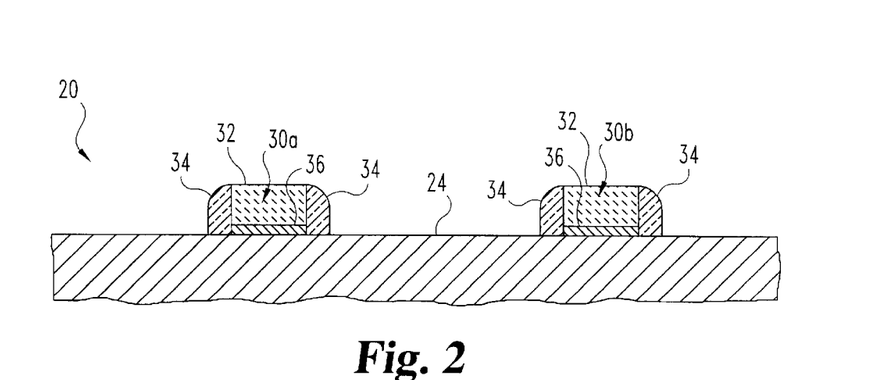
FIGS. 2 and 3 are schematic cross section illustrations of a generalized integrated circuit work piece at different processing stages.
Figure 3:
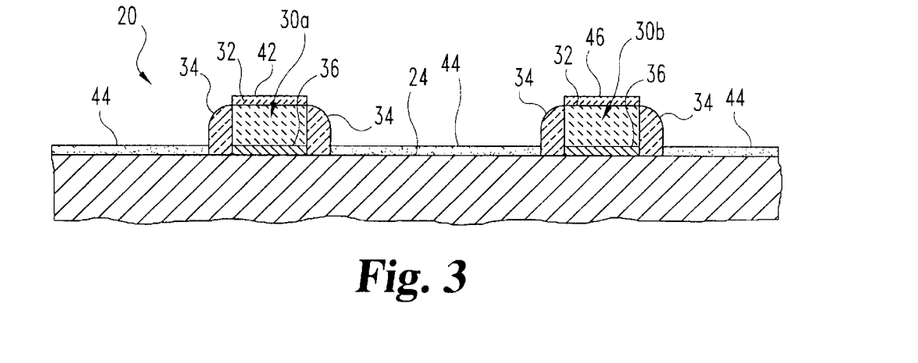

In another embodiment of this aspect of the invention, the substrate is an integrated circuit work piece. FIGS. 2 and 3 (not to scale) illustrate by way of example, but without limitation, various processing stages of an integrated circuit work piece 20. FIG. 2 depicts work piece 20 before a selective coating process is performed. FIG. 3 depicts work piece 20 after performance of a selective coating process. Work piece 20 includes silicon wafer substrate 22 having a substrate surface 24. Work piece 20 has multiple insulated gate field effect transistors (IGFETs) 30a and 30b, each comprising a polysilicon gate member 32 bounded by a pair of dielectric spacers 34, and insulative gate pad 36. Work piece 20 is reacted, as for example, but without limitation, in a CVD method, with an organometallic compound of the present invention, whereby the metal of an organometallic material 42, 44, and 46 is deposited on the piece as shown in FIG. 3. The metal or metal containing material 42, 44, and 46 may be selectively deposited on the silicon substrate surfaces 24 and on the surfaces of the polysilicon gate members 32, or may be blanket deposited over the entire workpiece surface and then selectively removed to leave the depicted pattern of metal or metal containing material 42, 44, and 46 only on the silicon substrate surfaces 24 and the surfaces of the polysilicon gate members 32 by any number of methods well known in the art.

In a preferred embodiment, the metal containing material 42, 44, and 46 is a metal silicide formed by annealing a metal film after deposition, or by co-deposition of a metal with silane, disilane or other silicon CVD precursor compound.

It should be appreciated that in other embodiments, more or fewer integrated circuit devices can be involved, and that alternatively or additionally, other types of integrated circuit devices can be processed in accordance with the present invention, including, but not limited to, resisters, capacitors, bipolar junction transistors, diodes, and the like. Also, metal containing compounds can be applied to other types of substrates such as those directed to micro-machinery fabrication. In yet other embodiments, different substrates and/or IGFET compositions and deposition techniques other than CVD can be alternatively or additionally applied.

The following are examples of specific embodiments of the present invention and are illustrative of its principles. They are not to be considered restrictive, but merely representative of the broader invention disclosed.

EXAMPLE 1

Synthesis of Metal Precursor Compounds

All reactions and subsequent manipulations involving organometallic reagents were performed under argon or nitrogen atmosphere using Schlenk-type glassware and glovebox techniques. All solvents were freshly distilled from sodium under nitrogen. The phosphites were freshly distilled or sublimed under nitrogen. H-NMR spectra were recorded on a Varian™ U400 spectrometer.

Synthesis of $C_2H_5OP(OCH_3)_2$ and other Mixed Phosphites.

$PCl_3$ (0.1 mole) was added to 500 mL diethyl ether in a 2 L round-bottomed flask and cooled to −78° C. Dimethylaniline (0.10 mole) and ethanol (0.1 mole) were added slowly with stirring. Stirring continued for 2–3 hours. The reaction was recooled to −78° C. and dimethylaniline (0.20 moles) and methanol (0.20 moles) was added. The reaction mixture was warmed to room temperature and allowed to react with stirring for 2–3 hours. The resulting white precipitate was filtered and distilled under vacuum after removing the solvent.

The procedure was repeated with the appropriate alcohols to produce the following phosphites and mixed phosphites:

$(C_2H_5O)_2P(OCH_3)$,
$(C_2H_5O)_2P(O^iC_2H_9)$,
$(CH_3O)_2P(O^iC_3H_7)$,
$(CH_3O)_2P(O^nC_3H_7)$,
$(CH_3O)_2P(O^nC_4H_9)$,
$(CH_3O)_2P(OCH_2C_6H_5)$,
$(CH_3O)_2P(OC_6H_5)$,
$P(OCH_3)_3$, $P(OC_2H_5)_3$, $P(OCH(CH_3)_2)_3$, $P(OC_4H_9)_3$ and $(CH_3)_3SiOP(OCH_3)_2$ were purchased from Aldrich.

Synthesis of Metal Complexes

The corresponding cobalt complexes were then synthesized as follows:

60 mmoles of the phosphite product from above was added to 15 mmoles (2.0 g) $CoCl_2$ in 30 ml 2-methoxyethyl ether (diglyme) under nitrogen and stirred. The solution was cooled to $-78°$ C. and 20 mmoles $NaBH_4$ (3.0 g) was added to the mixture. The mixture was allowed to warn slowly to room temperature over 4 hours with stirring, and then stirred for an additional 2 hours. The solvent was removed in vacuo, followed by extraction with hexane. The hexane extracts were eluted with hexane through a chromatographic column of neutral alumina.

The product cobalt precursor compounds were identified by H-NMR. The precursors were further purified before use by sublimation or distillation at between about 70–120° C. and between about 0.02–0.50 mm Hg. The onset of sublimation for $HCo[(OCH_3)P(OC_2H_5)_2]_4$ was around 70° C., however, the bath temperature was raised to 120° C. to increase the sublimation rate. $HCo[(OCH_3)P(OC_2H_5)_2]_4$, $HCo[P(OCH_3)_3]_4$, $HCo[P(OC_2H_5)_3]_4$, $HCo[P(OCH(CH_3)_2)_3]_4$, and $HCo[P(OC_4H_9)_3]_4$ were sublimed without leaving significant residue. This indicated higher vapor pressure as well as better thermal stability of the former compared to the latter precursors. The liquid $HCo[(OC_6H_5)P(OCH_3)_2]_4$ required higher vacuum for the distillation and therefore was not distilled before use.

Metal complexes of manganese, technetium, rhenium, iron, ruthenium, osmium, rhodium, iridium, nickel, palladium and platinum can be prepared and characterized utilizing the general procedure described above.

Synthesis of Metal Silylphosphites 12.13 mL of dimethyltrimethylsilylphosphite was added to 2.0 g $CoCl_2$ in 30 ml diethylene glycol dimethyl ether under nitrogen and stirred. The solution was cooled to $-78°$ C. and 3.0 g $NaBH_4$ was added to the mixture. The mixture was warmed slowly to room temperature over 4 hours and then stirred for an additional 2 hours. The solvent was removed in vacuo, followed by extraction with hexane. The hexane extracts were eluted with hexane through a chromatographic column of neutral alumina. A liquid product was isolated in approximately 80% yield. The product was identified as $HCo[(CH_3)_3SiOP(OCH_3)_2]_4$ by H-NMR.

Metal silylphosphites of manganese, technetium, rhenium, iron, ruthenium, osmium, rhodium, iridium, nickel, palladium and platinum can be prepared and isolated utilizing this same general procedure.

EXAMPLE 2

Use of Metal Precursor Compounds in CVD

The cobalt precursor compounds from Example 1 were used to produce cobalt films on silicon wafers by CVD as summarized in Table 1. For each deposition, a silicon wafer was placed in the reaction chamber of a CVD unit, and the system was purged with argon gas. The reactor was then evacuated to $10^{-6}$ mm Hg, and the wafer was heated to the stated temperature. The precursor vessel was maintained at the stated temperature. Deposition was conducted for the stated times. During the deposition, the reaction chamber pressure was maintained at 0.05 mm Hg when no carrier gas was used or at 5.0 mm Hg when argon or hydrogen was used. Pressures ranging from 0.1 to 10 mm Hg or higher have generally been preferred when a carrier gas is used.

The depositions resulted in cobalt films being deposited. Deposition of $HCO[P(OC_2H_5)_3]_4$ for 12 minutes with a substrate temperature of 300° C., 0.5 mm Hg, and no carrier gas, resulted in a cobalt film measured at 1600–1800 nm thickness.

Organometallic precursor compounds based on manganese, technetium, rhenium, iron, ruthenium, osmium, rhodium, iridium, nickel, palladium, and platinum according to Example 1 can be used to produce metal films on silicon wafers in a similar manner.

TABLE 1

| Precursor | Substrate Temp. | Feed Temp | Deposition Time |
|---|---|---|---|
| $HCo[P(OCH_3)_3]_4$ | 230 | 140 | 15 |
| | 240 | 130 | 15 |
| | 260 | 130 | 15 |
| | 265 | 100 | 75 |
| | 280 | 130 | 15 |
| $HCo[P(OC_2H_5)_3]_4$ | 250 | 130 | 12 |
| | 275 | 130 | 12 |
| | 300 | 130 | 12 |
| | 400 | 120 | 20 |
| | 500 | 120 | 10 |
| $HCo[P(OCH(CH_3)_2)_3]_4$ | 140 | 118 | 30 |
| | 160 | 118 | 30 |
| | 175 | 118 | 30 |
| | 210 | 118 | 30 |
| $HCo[P(OC_4H_9)_3]_4$ | 270 | 150 | 30 |
| | 280 | 150 | 30 |
| | 295 | 150 | 30 |
| | 310 | 150 | 30 |
| $HCo[(CH_3)_3SiOP(OCH_3)_2]_4$ | 150 | 50 | 30 |

EXAMPLE 3

Integrated Circuit Device Having a Cobalt Film

An integrated circuit work piece is provided with a blanket film of cobalt as follows: An integrated circuit work piece is cleaned by standard procedures and placed in a CVD reactor. The reaction chamber is evacuated and backfilled with argon, $HCo[(CH_3)_3SiOP(OCH_3)_2]_4$ is maintained at 50° C. in the reagent source chamber. The integrated circuit work piece is heated to 150° C. $HCo[(CH_3)_3SiOP(OCH_3)_2]_4$ vapor is fed into the reaction chamber at 50° C. and 0.2 mm Hg pressure for 30 minutes. The vapor feed is replaced with a pure argon feed to flush remaining decomposition by-products from the chamber and the coated work piece is cooled to room temperature. A layer of cobalt greater than 1800 nm thick is deposited on the surface of the integrated circuit work piece and is essentially free of carbon and oxygen contamination.

Additional integrated circuit devices having a metal film derived from manganese, technetium, rhenium, iron, ruthenium, osmium, rhodium, iridium, nickel, palladium, and platinum free of oxygen and carbon can be prepared according to Example 3 utilizing the organometallic precursors described herein.

While the invention has been described in detail in the foregoing description, the same is to be considered as illustrative and not restrictive in character, it being understood that only the preferred embodiments have been described and that all changes and modifications that come within the spirit of the invention are desired to be protected.

What is claimed is:

1. An organometallic compound of the formula $(R^1)_m M (PR^2{}_3)_x$, where M is a metal selected from the group consisting of manganese, technetium, rhenium, iron, ruthenium, osmium, nickel, palladium, and platinum; each $R^1$ is independently selected from the group consisting of hydrogen, deuterium, $H_2$, $D_2$ and a group of the formula $—CR^3{}_2—CR^3{}_2—R^4$, each $R^2$ is independently selected from the group consisting alkoxy, aryloxy, arylalkyl, arylalkoxy, alkylsilyl, arylsilyl, arylalkylsilyl, alkoxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy; each $R^3$ is independently selected from the group consisting of hydrogen, deuterium, $C_1$–$C_6$ alkyl, $C_1$–$C_6$ cycloalkyl, phenyl, benzyl, ($C_1$–$C_2$ alkyl or alkoxy)$_3$-silyl, and ($C_1$–$C_2$ alkyl or alkoxy)$_3$-siloxy and wherein at least two groups $R^3$ are selected from the group consisting of hydrogen and deuterium; $R^4$ is hydrogen or deuterium; and wherein (a) when M is manganese, technetium or rhenium, m is 1; x is 5 and m+x is 6 and wherein said $R^2$ groups are not all the same; and (b) when M is iron, ruthenium or osmium m is 0, 1, 2, 3 or 4; x is 2, 3, 4 or 5 and m+x is 4, 5, 6 or 7; and wherein said $R^2$ groups are not all the same; and (c) when M is nickel, palladium or platinum m is 0 or 2, x is 2, 3 or 4 and m+x is 2, 3, 4, 5 or 6; and wherein said $R^2$ groups are not all the same.

2. The compound of claim 1 wherein M is iron, ruthenium or osmium, $R^1$ is hydrogen and the compound is selected from the group consisting of $H_2M[(C_6H_5)OP(OCH_3)_2]_4$, $H_2M[(C_6H_5)OP(OC_2H_5)_2]_4$, $H_2M[(CH_2OP(OCH_3)_2]_4$, $H_2M[(C_6H_5)CH_2OP(OC_2H_5)_2]_4$, $H_2M[(C_3H_7)OP(OCH_3)_2]_4$, $H_2M[(C_4H_9)OP(OC_2H_5)_2]_4$, $H_2M[(CH_3)OP(OC_2H_5)_2]_4$, $H_2M[(H_2H_5)OP(OCH_3)_2]_4$, $H_2M[(C_4H_9)OP(OCH_3)_2]_4$, $M[(C_6H_5)OP(OCH_3)_2]_5$, $M[(C_6H_5)OP(OC_2H_5)_2]_5$, $M[(C_6H_5)CH_2OP(OCH_3)_2]_5$, $M[(C_6H_5)CH_2OP(OC_2H_5)_2]_5$, $M[(C_3H_7)OP(OCH_3)_2]_5$, $M[(C_4H_9)OP(OC_2H_5)_2]_5$, $M[(CH_3)OP(OC_2H_5)_2]_5$, $M[(C_2H_5)OP(OCH_3)_2]_5$, and $M[(C_4H_9)OP(OCH_3)_2]_5$.

3. The compound of claim 1 wherein M is nickel, palladium or platinum, m is 0 and the compound is selected from the group consisting of $M[(C_6H_5)OP(OCH_3)_2]_4$, $M[(C_6H_5)OP(OC_2H_5)_2]_4$, $M[(C_6H_5)CH_2OP(OCH_3)_2]_4$, $M[(C_6H_5)CH_2OP(OC_2H_5)_2]_4$, $M[(C_3H_7)OP(OCH_3)_2]_4$, $M[(C_4H_9)OP(OC_2H_5)_2]_4$, $M[(CH_3)OP(OC_2H_5)_2]_4$, $M[(C_2H_5)OP(OCH_3)_2]_4$, $M[(C_4H_9)OP(OCH_3)_2]_4$, $M[(C_6H_5)OP(OCH_3)_2]_3$, $M[(C_6H_5)OP(OC_2H_5)_2]_3$, $M[(C_6H_5)CH_2OP(OCH_3)_2]_3$, $M[(C_6H_5)CH_2OP(OC_2H_5)_2]_3$, $M[(C_3H_7)OP(OCH_3)_2]_3$, $M[(C_4H_9)OP(OC_2H_5)_2]_3$, $M[(CH_3)OP(OC_2H_5)_2]_3$, $M[(C_2H_5)OP(OCH_3)_2]_3$, $M[(C_4H_9)OP(OCH_3)_2]_3$, $M[(C_6H_5)OP(OCH_3)_2]_2$, $M[(C_6H_5)OP(OC_2H_5)_2]_2$, $M[(C_6H_5)CH_2OP(OCH_3)_2]_2$, $M[(C_6H_5)CH_2OP(OC_2H_5)_2]_2$, $M[(C_3H_7)OP(OCH_3)_2]_2$, $M[(C_4H_9)OP(OC_2)_2$, $M[(CH_3)OP(OC_2H_5)_2]_2$, $M[(C_2H_5)OP(OCH_3)_2]_2$, and $M[(C_4H_9)OP(OCH_3)_2]_2$.

4. An organometallic compound of the formula $(R^1)_m M (PR^2{}_3)_x$, where M is a metal selected from the group consisting of rhodium and iridium; m is 1, 3 or 4; x is 2, 3 or 4; and m+x is 4, 5, 6, 7 or 8; each $R^1$ is independently selected from the group consisting of hydrogen, deuterium, $N_2$, $H_2$, $D_2$ and a group of the formula $—CR^3{}_2—CR^3{}_2—R^4$; each $R^2$ is independently selected from the group consisting of arylalkyl, alkoxy, aryloxy, arylalkoxy, alkylsilyl, arylsilyl, arylalkylsilyl, alkoxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy; each $R^3$ is independently selected from the group consisting of hydrogen, deuterium, $C_1$–$C_6$ alkyl, $C_1$–$C_6$ cycloalkyl, phenyl, benzyl, ($C_1$–$C_2$ alkyl or alkoxy)$_3$-silyl, and ($C_1$–$C_2$ alkyl or alkoxy)$_3$-siloxy and wherein at least two groups $R^3$ are selected from the group consisting of hydrogen and deuterium; $R^4$ is hydrogen or deuterium; and wherein said $R^2$ groups are not all the same.

5. The compound of claim 4 wherein M is rhodium, $R^1$ is hydrogen and the compound is selected from the group consisting of $HRh[(C_6H_5)OP(OCH_3)_2]_4$, $HRh[(C_6H_5)OP(OC_2H_5)_2]_4$, $HRh[(C_6H_5)CH_2OP(OCH_3)_2]_4$, $HRh[(C_6H_5)CH_2OP(OC_2H_5)_2]_4$, $HRh[(C_3H_7)OP(OCH_3)_2]_4$, $HRh[(C_4H_9)OP(OC_2H_5)_2]_4$, $HRh[(CH_3)OP(OC_2H_5)_2]_4$, $HRh[(C_2H_5)OP(OCH_3)_2]_4$, and $HRh[(C_4H_9)OP(OCH_3)_2]_4$.

6. The compound of claim 4 wherein M is iridium, $R^1$ is hydrogen and the compound is selected from the group consisting of $H_3Ir[(C_6H_5)OP(OCH_3)_2]_3$, $H_3Ir[(C_6H_5)OP(OC_2H_5)_2]_3$, $H_3Ir[(C_6H_5)CH_2OP(OCH_3)_2]_3$, $H_3Ir[(C_6H_5)CH_2OP(OC_2H_5)_2]_3$, $H_3Ir[(C_3H_7)OP(OCH_3)_2]_3$, $H_3Ir[(C_4H_9)OP(OC_2H_5)_2]_3$, $H_3Ir[(CH_3)OP(OC_2H_5)_2]_3$, $H_3Ir[(C_2H_5)OP(OCH_3)_2]_3$, $H_3Ir[(C_4H_9)OP(OCH_3)_2]_3$, $H_5Ir[(C_6H_5)OP(OC_2H_5)_2]_2$, $H_5Ir[(C_6H_5)CH_2OP(OCH_3)_2]_2$, $H_5Ir[(C_6H_5)CH_2OP(OC_2H_5)_2]_2$, $H_5Ir[(C_3H_7)OP(OCH_3)_2]_2$, $H_5Ir[(C_4H_9)OP(OC_2H_5)_2]_2$, $H_5Ir[(CH_3)OP(OC_2H_5)_2]_2$, $H_5Ir[(C_2H_5)OP(OCH_3)_2]_2$, $H_5Ir[(C_4H_9)OP(OCH_3H_3)_2]_2$.

7. A cobalt organometallic compound of the formula $(R^1)_m Co(PR^2{}_3)_x$, where m is 1, 2, or 3; x is 3 or 4; m+x is 5 or 6; each $R^1$ is independently selected from the group consisting of hydrogen, deuterium, $N_2$, $H_2$, $D_2$ and a group of the formula $—CR^3{}_2—CR^3{}_2—R^4$; each $R^2$ is independently selected from the group consisting of arylalkyl, alkoxy, aryloxy, arylalkoxy, alkylsilyl, arylsilyl, arylalkylsilyl, alkoxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy; each $R^3$ is independently selected from the group consisting of hydrogen, deuterium, $C_1$–$C_6$ alkyl, $C_1$–$C_6$ cycloalkyl, phenyl, benzyl, ($C_1$–$C_2$ alkyl or alkoxy)$_3$-silyl, and ($C_1$–$C_2$ alkyl or alkoxy)$_3$-siloxy and wherein at least two groups $R^3$ are selected from the group consisting of hydrogen and deuterium; $R^4$ is hydrogen or deuterium; and wherein when one group $R^1$ is selected to be $N_2$, then m is 2 and the second group $R^1$ is hydrogen or deuterium; and wherein said $R^2$ groups are not all the same.

8. The compound of claim 6 wherein $R^1$ is hydrogen and the compound is selected from the group consisting of HCo[($C_6H_5$)OP(OCH$_3$)$_2$]$_4$, HCo[($C_6H_5$)OP(OC$_2$H$_5$)$_2$]$_4$, HCo[($C_6H_5$)CH$_2$OP(OCH$_3$)$_2$]$_4$, HCo[($C_6H_5$)CH$_2$OP(OC$_2$H$_5$)$_2$]$_4$, HCo[($C_3H_7$)OP(OCH$_3$)$_2$]$_4$, HCo[($C_4H_9$)OP(OC$_2$H$_5$)$_2$]$_4$, HCo[(CH$_3$)OP(OC$_2$H$_5$)$_2$]$_4$, HCo[(C$_1$H$_5$)OP(OCH$_3$)$_2$]$_4$, and HCo[(C$_4$H$_9$)OP(OCH$_3$)$_2$]$_4$.

9. The compound of claim 1 wherein at least one of $R^2$ is selected from the group consisting of alkylsilyl, arylsilyl, arylalkylsilyl, alkoxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy.

10. The compound of claim 9 wherein M is iron, ruthenium, or osmium and the compound is selected from the group consisting of H$_2$M[(CH$_3$)$_3$SiOP(OCH$_3$)$_2$]$_4$, H$_2$M[(CH$_3$)$_3$SiOP(OC$_2$H$_5$)$_2$]$_4$, H$_2$M[(C$_2$H$_5$)$_3$SiOP(OCH$_3$)$_2$]$_4$, H$_2$M[(C$_2$H$_5$)$_3$SiOP(OC$_2$H$_5$)$_2$]$_4$, M[(CH$_3$)$_3$SiOP(OCH$_3$)$_2$]$_5$, M[(CH$_3$)$_3$SiOP(OC$_2$H$_5$)$_2$]$_5$, M[(C$_2$H$_5$)$_3$SiOP(OCH$_3$)$_2$]$_5$, and M[(C$_2$H$_5$)$_3$SiOP(OC$_2$H$_5$)$_2$]$_5$.

11. The compound of claim 9 wherein M is nickel, palladium or platinum and the compound is selected from the group consisting of M[(CH$_3$)$_3$SiOP(OCH$_3$)$_2$]$_4$, M[(CH$_3$)$_3$SiOP(OC$_2$H$_5$)$_2$]$_4$, M[(C$_2$H$_5$)$_3$SiOP(OCH$_3$)$_2$]$_4$, and M[(C$_2$H$_5$)$_3$SiOP(OC$_2$H$_5$)$_2$]$_4$.

12. The compound of claim 4 wherein at least one of $R^2$ is selected from the group consisting of alkylsilyl, arylsilyl, arylalkylsilyl, alkoxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy.

13. The compound of claim 12 wherein M is rhodium and the compound is selected from the group consisting of HRh[(CH$_3$)$_3$SiOP(OCH$_3$)$_2$]$_4$, HRh[(CH$_3$)$_3$SiOP(OC$_2$H$_5$)$_2$]$_4$, HRh[(C$_2$H$_5$)$_3$SiOP(OCH$_3$)$_2$]$_4$, HRh[(C$_2$H$_5$)$_3$SiOP(OC$_2$H$_5$)$_2$]$_4$.

14. The compound of claim 12 wherein M is iridium and the compound is selected from the group consisting of H$_3$Ir[(CH$_3$)$_3$SiOP(OCH$_3$)$_2$]$_3$, H$_3$Ir[(CH$_3$)$_3$SiOP(OC$_2$H$_5$)$_2$]$_3$, H$_3$Ir[(C$_2$H$_5$)$_3$SiOP(OCH$_3$)$_2$]$_3$, H$_3$Ir[(C$_2$H$_5$)$_3$SiOP(OC$_2$H$_5$)$_2$]$_3$, H$_5$Ir[(CH$_3$)$_3$SiOP(OCH$_3$)$_2$]$_2$, H$_5$Ir[(CH$_3$)$_3$SiOP(OC$_2$H$_5$)$_2$]$_2$, H$_5$Ir[(C$_2$H$_5$)$_3$SiOP(OCH$_3$)$_2$]$_2$, and H$_5$Ir[(C$_2$H$_5$)$_3$SiOP(OC$_2$H$_5$)$_2$]$_2$.

15. The compound of claim 7 wherein at least one of $R^2$ is selected from the group consisting of alkylsilyl, arylsilyl, arylalkylsilyl, alkoxysilyl, aryloxysilyl, arylalkoxysilyl, alkylsiloxy, arylsiloxy, arylalkylsiloxy, alkoxysiloxy, aryloxysiloxy, arylalkoxysiloxy, alkylsilylalkyl, arylsilylalkyl, arylalkysilylalkyl, alkoxysilylalkyl, aryloxysilylalkyl, arylalkoxysilylalkyl, alkylsiloxyalkyl, arylsiloxyalkyl, arylalkylsiloxyalkyl, alkoxysiloxyalkyl, aryloxysiloxyalkyl, arylalkoxysiloxyalkyl, alkylsilylalkoxy, arylsilylalkoxy, arylalkylsilylalkoxy, alkoxysilylalkoxy, aryloxysilylalkoxy arylalkyloxysilylalkoxy, alkylsiloxyalkoxy, arylsiloxyalkoxy, arylalkylsiloxyalkoxy, alkoxysiloxyalkoxy, aryloxysiloxyalkoxy, and arylalkoxysiloxyalkoxy.

16. The compound of claim 15 wherein the compound is selected from the group consisting of HCo[(CH$_3$)$_3$SiOP(OCH$_3$)$_2$]$_4$, HCo[(CH$_3$)$_3$SiOP(OC$_2$H$_5$)$_2$]$_4$, HCo[(C$_2$H$_5$)$_3$SiOP(OCH$_3$)$_2$]$_4$, and HCo[(C$_2$H$_5$)$_3$SiOP(OC$_2$H$_5$)$_2$]$_4$.

* * * * *

UNITED STATES PATENT AND TRADEMARK OFFICE
CERTIFICATE OF CORRECTION

PATENT NO.     : 6,777,565 B2
DATED          : August 17, 2004
INVENTOR(S)    : Hyungsoo Choi It is certified that error appears in the above-identified patent and that said Letters Patent is hereby corrected as shown below:

Title page,
Item [56], References Cited, U.S. PATENT DOCUMENTS, please change "5,587,561 A 12/1996 Berkcan et al." to -- 5,567,651 A 10/1996 Berti et al. --.
FOREIGN PATENT DOCUMENTS, "GB 717269" reference, please change date from "2/1954" to -- 10/1954 --.
OTHER PUBLICATIONS, "Gosser, L.W.," reference, please change "Hydridoacaloniriletris" should read -- Hydridoacetoniriletris --.
"Carlton, Laurence," reference, please change "Rh2(.mu.-SC8F5)2(PPh3)4" to -- Rh2(.mu.-SC6F5)2(PPh3)4 --.
"Muetterties, E.L. et al." reference, please change "pp. 4685-4687" to -- pp. 4665-4667 --.
"Muetterties, E.L." reference, second occurrence, please change "phosphiles" to -- phosphites --.
"Barefield, E.K.," reference, please change "pp. 5234-5236" to -- pp. 5234-5235 --.
"Titus, D.D.," reference, please change "cobelt" to -- cobalt --; and please change "pp. 3622-323" to -- pp. 322-323 --.
"Lane, P.A.," reference, please change "pp. 183-188" to -- pp. 183-186 --.
"Gerlach, D.H.," reference, please change "Tel-rakis" to -- Tet-rakis --.
"Smith, K.C.," reference, please change "No. 378" to -- No. 376 --.
"Titus, D.," reference, please change "Diathyl" to -- Diethyl --.

Column 19,
Line 46, please change "$H_2M[(CH_2OP(OCH_3)_2]_4$" to -- $H_2M[(C_6H_5)(CH_2OP(OCH_3)_2]_4$ --.
Line 49, please change "$H_2M[(H_2H_5)OP(OCH_3)_2]_4$" to -- $H_2M[(C_2H_5)OP(OCH_3)_2]_4$ --

Column 20,
Line 2, please change "$M[(C_4H_9)OP(OC_2]_2$" to -- $M[(C_4H_9)OP(OC_2H_5)_2]_2$ --.

Column 21,
Line 8, please change "claim 6" to -- claim 7 --.
Line 13, please change "$HCo[(C_1H_5)OP$" to -- $HCo[(C_2H_5)OP$ --.
Line 34, please change "$M[(C_2H_5)_3SiOP(OCH_3)_2]_5$" to -- $M[(C_2H_5)_3SiOP(OCH_3)_2]_5$ --.

UNITED STATES PATENT AND TRADEMARK OFFICE
CERTIFICATE OF CORRECTION

PATENT NO.   : 6,777,565 B2
DATED        : August 17, 2004
INVENTOR(S)  : Hyungsoo Choi It is certified that error appears in the above-identified patent and that said Letters Patent is hereby corrected as shown below:

<u>Column 22,</u>
Line 14, after "$HRh[(C_2H_5)_3SiOP(OCH_3)_2]_4$," please add -- and --.

Signed and Sealed this

Second Day of November, 2004

JON W. DUDAS
*Director of the United States Patent and Trademark Office*